United States Patent [19]

Dunn et al.

[11] Patent Number: 5,220,021
[45] Date of Patent: Jun. 15, 1993

[54] GEMINAL BISPHOSPHONIC ACIDS AND DERIVATIVES AS ANTI-ARTHRITIC AGENTS

[75] Inventors: Colin J. Dunn, Richland; Richard A. Nugen, Galesburg, both of Mich.

[73] Assignee: The Upjohn Company, Kalamazoo, Mich.

[21] Appl. No.: 761,733

[22] PCT Filed: Mar. 8, 1990

[86] PCT No.: PCT/US90/01106
§ 371 Date: Sep. 6, 1991
§ 102(e) Date: Sep. 6, 1991

Related U.S. Application Data

[63] Continuation-in-part of Ser. No. 332,618, Apr. 3, 1989, abandoned.

[51] Int. Cl.$^5$ ............... C07D 413/02; C07D 9/28; C07F 9/06
[52] U.S. Cl. ................. 544/140; 544/243; 546/22; 546/23; 546/24; 548/101; 548/111
[58] Field of Search ............ 548/101, 111; 544/243, 544/140; 546/23, 22, 24

[56] References Cited

U.S. PATENT DOCUMENTS 3,683,080  8/1972  Francis ..................... 424/204
4,746,654  5/1988  Breliere .................... 514/108

FOREIGN PATENT DOCUMENTS

51534/85  12/1985  Australia .
0304962  12/1985  European Pat. Off. .
0282320   3/1988  European Pat. Off. .
3719513A  6/1987  Fed. Rep. of Germany .
3719513  12/1988  Fed. Rep. of Germany .

OTHER PUBLICATIONS

CA 111:23604z Diastereofacial . . . oxide, Brandi et al. p. 626 1989.
CA 112:112068r Preparation of . . . diseases, Schwab et al. p. 73 1990.
CA 114:122364q Preparation of . . . regulators, Dunn et al. p. 799, 1991.
CA 115:223031e Effect of . . . bacteria, Dickneite et al. p. 48, 1991.
Khusainova, N. G., and Pudovik, A. N., Russian Chemical Reviews, 47(9):803–813 (1978).

*Primary Examiner*—Mary C. Lee
*Assistant Examiner*—Joseph K. McKane
*Attorney, Agent, or Firm*—Bruce Stein

[57] ABSTRACT

Unsaturated geminal phosphonates (III)

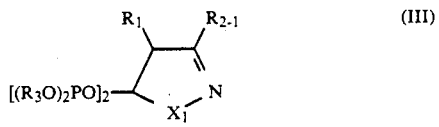

either as the esters, free acids or salts are useful in the treatment of arthritis.

12 Claims, No Drawings

GEMINAL BISPHOSPHONIC ACIDS AND DERIVATIVES AS ANTI-ARTHRITIC AGENTS

BACKGROUND OF THE INVENTION

This application is a continuation in part of 07/332,618 filed Apr. 3, 1989, now abandoned.

1. Field of the Invention

The invention is geminal phosphonic acids, esters and salts which are useful as anti-arthritic agents.

2. Description of the Related Art

Russian Chemical Reviews 47, 803 (1978) disclose 1,3-dipolar cycloaddition to unsaturated organophosphorus compounds to form five member heterocycles which contain a phosphorus atom in a side-chain such as phosphinyl-$\Delta^2$-pyrazolines, 5-phosphinyl-2-isoxazolines, isoxazolidines.

U.S. Pat. No. 4,746,654 discloses bisphosphonates useful as anti-inflammatory agents.

Australian Patent A-51534/85 discloses bisphosphonates useful in treating abnormal calcium and phosphorus metabolism and useful in treating arthritis.

U.S. Pat. No. 3,683,080 discloses polyphosphonates, in particular diphosphonates useful in inhibiting anomalous deposition and mobilization of calcium phosphate in animal tissue.

DE 3,719,513-A (Derwent 89-000580/01) discloses diphosphonic acid derivatives useful in treatment of disorders of calcium metabolism. while the generic formula for these compounds seems similar to those of the claimed invention, by their definition the compounds of the present invention are prohibited.

SUMMARY OF INVENTION

Disclosed is an unsaturated geminal phosphonate of formula (III) where $X_1$ is —O—, —NH— or —N—metal where metal is sodium, potassium, calcium, magnesium, copper, zinc, barium, silver and gold;

$R_1$ is —H, $C_1$-$C_4$ alkyl, $C_3$-$C_7$ cycloalkyl, -$\phi$ optionally substituted with 1 through 5 —F, —Cl, —Br, —I, —CF$_3$, $C_1$-$C_6$ alkyl, $C_1$-$C_6$ cycloalkyl, $C_1$-$C_4$ alkoxy or $C_1$-$C_4$ alkylthio;

$R_{2\text{-}1}$ is
$C_1$-$C_6$ alkyl,
$C_3$-$C_7$ cycloalkyl,
-$\phi$ optionally substituted with 1 through 5 —F, —Cl, —Br, —I, —NO$_2$, —CN, —CF$_3$, $C_1$-$C_6$ alkyl, $C_3$-$C_7$ cycloalkyl, $C_1$-$C_4$ alkoxy, $C_1$-$C_4$ alkylthio,
—CH(OH)—$R_{2\text{-}5}$ where $R_{2\text{-}5}$ is
- (A) $C_1$-$C_{10}$ alkyl,
- (B) $C_3$-$C_7$ cycloalkyl,
- (C) -$\phi$ optionally substituted with 1 or 2 -$\phi$ or 1 through 5 —F, —Cl, —Br, —I, —NO$_2$, —CN, —CF$_3$, $C_1$-$C_6$ alkyl, $C_3$-$C_7$ cycloalkyl, $C_1$-$C_4$ alkoxy, $C_1$-$C_4$ alkylthio,
- (D) 2- and 3-furanyl optionally substituted with 1 through 3 —F, —Cl, —Br, —I, —NO$_2$, —CN, —CF$_3$, $C_1$-$C_6$ alkyl, $C_3$-$C_7$ cycloalkyl, $C_1$-$C_4$ alkoxy, —O-$\phi$, $C_1$-$C_4$ alkylthio,
- (E) 2-, 4- and 5-pyrimidyl optionally substituted with 1 through 3 —F, —Cl, —Br, —I, —NO$_2$, —CN, —CF$_3$, $C_1$-$C_6$ alkyl, $C_3$-$C_7$ cycloalkyl, $C_1$-$C_4$ alkoxy, $C_1$-$C_4$ alkylthio,
- (F) 2-, 3- and 4-pyridinyl optionally substituted with 1 through 4 —F, —Cl, —Br, —I, —NO$_2$, —CN, —CF$_3$, $C_1$-$C_6$ alkyl, $C_3$-$C_7$ cycloalkyl, $C_1$-$C_4$ alkoxy, $C_1$-$C_4$ alkylthio,
- (G) 2- and 3-thiophene optionally substituted with 1 through 3 —F, —Cl, —Br, —I, —NO$_2$, —CN, —CF$_3$, $C_1$-$C_6$ alkyl, $C_3$-$C_7$ cycloalkyl, $C_1$-$C_4$ alkoxy, $C_1$-$C_4$ alkylthio,
- (H) 1- and 2-naphthalene optionally substituted with 1 through 7 —F, —Cl, —Br, —I, —NO$_2$, —CN, —CF$_3$, $C_1$-$C_6$ alkyl, $C_3$-$C_7$ cycloalkyl, $C_1$-$C_4$ alkoxy, $C_1$-$C_4$ alkylthio,
- (I) 2-, 3-, 4-, 6-, 7- and 8-quinoline,
- (J) 1-, 3-, 4-, 6-, 7- and 8-isoquinoline,
- (K) 2-, 3-, 4-, 5-, 6- and 7-benzothiophene,
- (L) 2-, 3-, 4-, 5-, 6- and 7-benzofuran,
- (M) —NR$_{2\text{-}6}$R$_{2\text{-}7}$ where $R_{2\text{-}6}$ and $R_{2\text{-}7}$ are the same or different and are $C_1$-$C_4$ alkyl,
  -$\phi$,
  —CO—$R_{2\text{-}8}$ wherein $R_{2\text{-}8}$ is $C_1$-$C_4$ alkyl or -$\phi$ optionally substituted with 1 —CH$_3$,
  —SO$_2$—$R_{2\text{-}8}$ where $R_{2\text{-}8}$ is as defined above and where $R_{2\text{-}6}$ and $R_{2\text{-}7}$ are taken together with the attached nitrogen atom to form a 4 through 8 member heterocyclic ring containing a nitrogen, oxygfen or sulfur heteroatom and 0 thru 3 double bonds, —CO—$R_{2\text{-}5}$ where $R_{2\text{-}5}$ is as defined above;

$R_3$ is —H, $C_1$-$C_6$ alkyl, -$\phi$ and pharmaceutically acceptable salts thereof.

DETAILED DESCRIPTION OF THE INVENTION

The nitrogen containing dipoles (I) are either known to those skilled in the art or can readily be prepared from known compounds by known methods. For a review of the synthesis of dipoles (I) see, 1,3 Dipolar Cycloaddition Chemistry, edited by Albert Padwa, NY, Wiley, 1984. It is preferred that $X_1$ is —NH—. With regard to $R_2\$-$1$ it is preferred that $R_{2\text{-}1}$ is —CO—$R_{2\text{-}5}$ and —CH(OH)—$R_{2\text{-}5}$. It is more preferred that $R_{2\text{-}1}$ is —CO-$\phi$ optionally substituted with —F, —Cl, —Br, —I, —CN, —CF$_3$, $C_1$-$C_4$ alkoxy, $C_1$-$C_4$ alkylthio, $C_1$-$C_4$ alkyl, —N(CH$_3$)$_2$, —N(CH$_2$CH$_3$)$_2$, morpholino, 1-, and 2-naphthalene, 2-thienyl, cyclopropyl and 2-, 3- and 4-pyridyl.

There are two preferred methods of preparing the nitrogen containing dipoles (I) when $X_1$ is —NH—. One is treating acyl halides or anhydrides with an ethereal solution of diazomethane. Alternatively, one treats methyl ketones with base and ethyl formate to prepare the aldehyde ketone or a salt thereof, and treating this with tosyl azide.

There are two preferred ways of preparing the nitrogen containing dipole (I) when $X_1$ is —O—. One is the in situ dehydration of a nitro containing compound by phenylisocyanate. Alternatively, a chloro oxime is treated with an organic base such as TEA or DBU to generate the nitrogen containing dipole (I) in situ.

The vinylidene diphosphonates (II) are either known to those skilled in the art or can readily be prepared from known compounds by known methods. See, Tetrahedron 30, 301 (1974) and for $R_1$=—H see J. Org. Chem., 51, 3488 (1986). It is preferred that $R_1$ be —H. The preferred group of geminal phosphonates include the compounds of EXAMPLES 1, 3, 5, 7, 9, 12, 14 and 16-25; more preferred are the compounds of EXAMPLES 1, 3, 5, 7, 9, 14 and 16-25. Another preferred group includes the compounds of EXAMPLES 26-81.

The reaction condensing the nitrogen containing dipoles (I) with the vinylidene diphosphonates (II) to produce the unsaturated geminal phosphonate (III) is well known to those skilled in the art. See, for example, 1,3-Dipolar Cycloaddition Chemistry, ibid. The nitrogen containing dipoles (I) are stirred with the vinylidene diphosphonates (II) in a non-polar solvent such as ether at about 20°-25° for about 18-36 hr. When $X_1$ is —NH—, the unsaturated geminal phosphonate (III) crystallizes out and is obtained by filtration. When $X_1$ is —O—, the product (III) is obtained by extraction and purification.

The unsaturated geminal phosphonates (III) are readily prepared where $R_2\$-\$1$ is —CO—$R_{2-5}$. These compounds can readily be converted to compounds where $R_2\$-\$1$ is —CH(OH)—$R_{2-5}$ by reaction with a weak reducing agent, such as sodium borohydride, as is well known to those skilled in the art.

The phosphonic esters, either the unsaturated geminal phosphonates (III) are cleaved to the corresponding free acids by methods well known to those skilled in the art, see Tetrahedron Letters 155, (1977). More particularly, the invention uses trimethyl silyl bromide in chloroform followed by treatment with water. The unsaturated geminal phosphonates (III) in the free acid form are readily converted to the corresponding salt forms by reaction with alkali metal hydroxides. There are four acidic —H on the phosphonate, and when $X\$1$ is —NH—, one on the —NH— for a total of five. Therefore, one can have a salt with 1 thru 5 cations. Any salt which is pharmaceutically acceptable is operable. Suitable salts include sodium, potassium, calcium, magnesium, nanganese, copper, gold, ethanolamine, diethanolamine, triethanolamine, zinc and THAM. Preferred salts include sodium, potassium, calcium, magnesium and manganese. More preferred are sodium, potassium and calcium.

The unsaturated geminal phosphonates (III) are useful as antiarthritic agents. The unsaturated geminal phosphonates (III) are useful in humans and lower animals in the treatment of diseases characterized by abnormal phosphate and calcium metabolism and as a treatment of inflammation. These diseases include osteoporosis, Paget's disease, periodontal disease, rheumatoid arthritis, osteoarthritis, chondrocalcinosis, septic arthritis, neuritis, bursitis, soft tissue mineralization disorders, ankylosing spondylitis, atherosclerosis, multiple myeloma of bone, metastatic bone disease, chronic granulomatous diseases and mitral valve calcification.

The unsaturated geminal phosphonates (III) can be administered orally, parenterally (intramuscularly, intravenously, subcutaneously or intraperitoneally), transdermally or intra-articularly or by suppository. The dose is about 0.1 mg/patient/day to about 1.0 gm/patient/day.

The unsaturated geminal phosphonates (III) can be used alone or in combination with other pharmaceuticals as is known to those skilled in the art. The exact route of administration, dose, frequency of administration, of a particular unsaturated geminal phosphonate (III), depends on the particular disease or condition, the severity of the disease or condition, the age, general physical condition, weight, other clinical abnormalities, etc., of the particular patient to be treated as is known to those skilled in the art.

For the diseases outlined above intermittent therapy is indicated, as well as continual daily therapy in order to achieve maximum efficacy as is known to those skilled in the art. See, for example, "Long-Term Effects of Dichloromethylene Diphosphonate in Paget's Disease of Bone," P. D. Dumas, et al., J. Clin. Endocrinol. Metab., 54, 837 (1982); "Paget's Disease of Bone Treated in Five Days with AHPrBP(APD) Per Os," D. Thiebaud, et al., J. Bone Min. Res., 2, 45 (1987); "A Single Infusion of the Bisphosphonate AHPrBP(APD) as Treatment of Paget's Disease of Bone," D. Thiebaud, et al., The Am. J. Med., 85, 207 (1988); "A Double Blind Placebo-controlled Trial of Diphosphonate (APD) Therapy in Rheumatoid Arthritis—Preliminary Results," S. H. Ralston, et al., Calcif. Int., 42, A23 (1988); "Treatment of Hypercalcemia of Malignancy with Intermittent Single Infusions of 3-Amino-1-hydroxypropylidene-1,1-biphosphonate (APD)," D. Rischin, et al., Aust. NZ. J. Med., 18, 736 (1988); "Reduced Morbidity from Skeletal Metastases in aBreast Cancer Patients During Long-Term Bisphosphonate (APD) Treatment," A. Th. van Holten-Verzantvoort, et al., The Lancet, 10-31-87, p. 983; "Sclerosis of Lytic bone Metastases after Disodium Aminohydroxypropylidene Bisphosphonate (APD) in Patients with Breast Carcinoma," A. R. Morton, et al., British Med. J., 297, 772 (1988); "Two Year Follow-up of Bisphosphonate (APD) Treatment in Steroid Osteoporosis," I. R. Reid, et al., The Lancet 11-12-88, p. 1144.

DEFINITIONS AND CONVENTIONS

The definitions and explanations below are for the terms as used throughout this entire document including both the specification and the claims.

I. CONVENTIONS FOR FORMULAS AND DEFINITIONS OF VARIABLES

The chemical formulas representing various compounds or molecular fragments in the specification and claims may contain variable substituents in addition to expressly defined structural features. These variable substituents are identified by a letter or a letter followed by a numerical subscript, for example, "$Z_1$" or "$R_i$" where "i" is an integer. These variable substituents are either monovalent or bivalent, that is, they represent a group attached to the formula by one or two chemical bonds. For example, a group $Z_1$ would represent a bivalent variable if attached to the formula $CH_3$-$C(=Z_1)$H. Groups $R_i$ and $R_j$ would represent monovalent variable substituents if attached to the formula $CH_3$-$CH_2$-$C(R_i)(R_j)H_2$. When chemical formulas are drawn in a linear fashion, such as those above, variable substituents contained in parentheses are bonded to the atom immediately to the left of the variable substituent enclosed in parentheses. When two or more consecutive variable substituents are enclosed in parentheses, each of the consecutive variable substituents is bonded to the immediately preceding atom to the left which is not enclosed in parentheses. Thus, in the formula above, both $R_i$ and $R_j$ are bonded to the preceding carbon atom.

Chemical formulas or portions thereof drawn in a linear fashion represent atoms in a linear chain. The symbol "—" in general represents a bond between two atoms in the chain. Thus, $CH_3$—O—$CH_2$—CH($R_i$)—$CH_3$ represents a 2-substituted-1-methoxypropane compound. In a similar fashion, the symbol "=" represents a double bond, e.g., $CH_2=C(R_i)$—O—$CH_3$, and the symbol "≡" represents a triple bond, e.g., HC≡C—CH($R_i$)—$CH_2$—$CH_3$. Carbonyl groups are represented in either one of two ways: —CO— or —C(=O)—, with the former being preferred for simplicity.

Chemical formulas of cyclic (ring) compounds or molecular fragments can be represented in a linear fashion. Thus, the compound 4-chloro-2-methylpyridine can be represented in linear fashion by N*=C(CH$_3$)—CH=CCl—CH=C*H with the convention that the atoms marked with an asterisk (*) are bonded to each other resulting in the formation of a ring. Likewise, the cyclic molecular fragment, 4-(ethyl)-1-1-piperazinyl can be represented by —N*—(CH$_2$)$_2$—N(C$_2$H$_5$)—CH$_2$—C*H$_2$.

A rigid cyclic (ring) structure for any compound herein defines an orientation with respect to the plane of the ring for substituents attached to each carbon atom of the rigid cyclic compound. For saturated compounds which have two substituents attached to a carbon atom which is part of a cyclic system, —C(X$_1$)(X$_2$)—, the two substituents may be in either an axial or equatorial position relative to the ring and may change between axial/equatorial. However, the position of the two substituents relative to the ring and each other remains fixed. While either substituent at times may lie in the plane of the ring (equatorial) rather than above or below the plane (axial), one substituent is always above the other. In chemical structural formulas depicting such compounds, a substituent (X$_1$) which is "below" another substituent (X$_2$) will be identified as being in the alpha ($\alpha$) configuration and is identified by a broken, dashed or dotted line attachment to the carbon atom, i.e., by the symbol " - - - " or " . . . ". The corresponding substituent attached "above" (X$_2$) the other (X$_1$) is identified as being in the beta ($\beta$) configuration and is indicated by an unbroken line attachment to the carbon atom.

When a variable substituent is bivalent, the valences may be taken together or separately or both in the definition of the variable. For example, a variable R$_8$ attached to a carbon atom as —C(=R$_i$)— might be bivalent and be defined as oxo or keto (thus forming a carbonyl group (—CO—) or as two separately attached monovalent variable substituents $\alpha$-R$_{i-j}$ and $\beta$-R$_{i-k}$. When a bivalent variable, R$_i$, is defined to consist of two monovalent variable substituents, the convention used to define the bivalent variable is of the form "$\alpha$-R$_{i-j}$:$\beta$-R$_{i-k}$" or some variant thereof. In such a case both $\alpha$-R$_{i-j}$ and $\beta$-R$_{i-k}$ are attached to the carbon atom to give —C-($\alpha$-R$_{i-j}$)($\beta$-R$_{i-k}$)—. For example, when the bivalent variable R$_6$, —C(=R$_6$)— is defined to consist of two monovalent variable substituents, the two monovalent variable substituents are $\alpha$-R$_{6-1}$:$\beta$-R$_{6-2}$, . . . $\alpha$-R$_{6-9}$: $\beta$-R$_{6-10}$, etc., giving —C($\alpha$-R$_{6-2}$)($\beta$-R$_{6-2}$)—, . . . —(C$\alpha$-R$_{6-9}$)($\beta$-R$_{6-10}$)—, etc. Likewise, for the bivalent variable R$_{11}$, —C(=R$_{11}$)—, two monovalent variable substituents are $\alpha$-R$_{11-1}$:$\beta$-R$_{11-2}$. For a ring substituent for which separate $\alpha$ and $\beta$ orientations do not exist (e.g., due to the presence of a carbon double bond in the ring), and for a substituent bonded to a carbon atom which is not part of a ring the above convention is still used, but the $\alpha$ and $\beta$ designations are omitted.

Just as a bivalent variable may be defined as two separate monovalent variable substituents, two separate monovalent variable substituents may be defined to be taken together to form a bivalent variable. For example, in the formula —C$_1$(R$_i$)H—C$_2$(R$_j$)H— (C$_1$ and C$_2$ define arbitrarily a first and second carbon atom, respectively) R$_i$ and R$_j$ may be defined to be taken together to form (1) a second bond between C$_1$ and C$_2$ or (2) a bivalent group such as oxa (—O—) and the formula thereby describes an epoxide. When R$_i$ and R$_j$ are taken together to form a more complex entity, such as the group —X—Y—, then the orientation of the entity is such that C$_1$ in the above formula is bonded to X and C$_2$ is bonded to Y. Thus, by convention the designation " . . . R$_i$ and R$_j$ are taken together to form —CH$_2$—CH$_2$—O—CO— . . . " means a lactone in which the carbonyl is bonded to C$_2$. However, when designated " . . . R$_j$ and R$_i$ are taken together to form —CO—O—CH$_2$—CH$_2$— . . . " the convention means a lactone in which the carbonyl is bonded to C$_1$.

The carbon atom content of variable substituents is indicated in one of two ways. The first method uses a prefix to the entire name of the variable such as "C$_1$-C$_4$", where both "1" and "4" are integers representing the minimum and maximum number of carbon atoms in the variable. The prefix is separated from the variable by a space. For example, "C$_1$-C$_4$ alkyl" represents alkyl of 1 through 4 carbon atoms (including isomeric forms thereof unless an express indication to the contrary is given). Whenever this single prefix is given, the prefix indicates the entire carbon atoms content of the variable being defined. Thus C$_2$-C$_4$ alkoxycarbonyl describes a group CH$_3$—(CH$_2$)$_n$—O—CO— where n is zero, one or two. By the second method the carbon atom content of only each portion of the definition is indicated separately by enclosing the "C$_i$-C$_j$" designation in parentheses and placing it immediately (no intervening space) before the portion of the definition being defined. By this optional convention (C$_1$-C$_3$)alkoxycarbonyl has the same meaning as C$_2$-C$_4$ alkoxycarbonyl because the "C$_1$-C$_3$" refers only to the carbon atom content of the alkoxy group. Similarly while both C$_2$-C$_6$ alkoxyalkyl and (C$_1$-C$_3$)alkoxy(C$_1$-C$_3$)alkyl define alkoxyalkyl groups containing from 2 to 6 carbon atoms, the two definitions differ since the former definition allows either the alkoxy or alkyl portion alone to contain 4 or 5 carbon atoms while the latter definition limits either of these groups to 3 carbon atoms.

II. DEFINITIONS

All temperatures are in degrees Centigrade.
TLC refers to thin-layer chromatography.
p-TSA refers to p-toluenesulfonic acid monohydrate.
TEA refers to triethylamine.
DBU refers to 1,8-diazabicyclo[5.4.0]undec-7-ene.
Saline refers to an aqueous saturated sodium chloride solution.
IR refers to infrared spectroscopy.
CMR refers to C-13 magnetic resonance spectroscopy, chemical shifts are reported in ppm ($\delta$) downfield from TMS.
NMR refers to nuclear (proton) magnetic resonance spectroscopy, chemical shifts are reported in ppm ($\delta$) downfield from tetramethylsilane.
-$\phi$ refers to phenyl (C$_6$H$_5$).
MS refers to mass spectrometry expressed as m/e or mass/charge unit . [M+H]$^+$ refers to the positive ion of a parent plus a hydrogen atom. EI refers to electron impact. CI refers to chemical ionization. FAB refers to fast atom bombardmen.
Ether refers to diethyl ether.
Pharmaceutically acceptable refers to those properties and/or substances which are acceptable to the patient from a pharmaceutical/toxicological point of view and to the manufacturing pharmaceutical chemist from a physical/chemical point of view regarding composition, formulation, stability, patient acceptance and bioavailability.

When solvent pairs are used, the ratios of solvents used are volume/volume (v/v).

EXAMPLES

Without further elaboration, it is believed that one skilled in the art can, using the preceding description, practice the present invention to its fullest extent. The following detailed examples described how to prepare the various compounds and/or perform the various processes of the invention and are to be construed as merely illustrative, and not limitations of the preceding disclosure in any way whatsoever. Those skilled in the art will promptly recognize appropriate variations from the procedures both as to reactants and as to reaction conditions and techniques.

PREPARATION 1

Ethenylidene Bisphosphonic Acid Tetraethyl Ester (II)

Paraformaldehyde (104.2 g) and diethylamine (50.8 g) are combined in methanol (2 l), warmed until clear, then treated with methylene bisphosphonic acid, tetraethyl ester (190.09 g) and refluxed for 18 hrs. The sample is then concentrated, methanol added, the methanol removed by heat and reduced pressure, toluene is added and removed by heat and reduced pressure. The residue is dissolved in toluene (1 l), treated with p-TSA (0.5 g) and refluxed through a Dean Stark trap for 18 hrs. The sample is concentrated under reduced pressure with heat, dissolved in methylene chloride washed twice with water, dried with magnesium sulfate, and concentrated under reduced pressure with heat. The sample is purified by distillation at reduced pressure to give the title compound, bp=140° (0.6 torr); MS (m/e) 300, 285, 273, 255, 245, 227, 217, 199, 192, 181, 163, 153 and 135; IR (neat) 2984, 2934, 2909, 1651, 1580, 1479, 1444, 1392, 1254, 1166, 1098, 1042, 1025, 974, 855, 813 and 800 $cm^{-1}$; NMR (CDCl$_3$) 7.1, 6.7, 4.1 and 1.3 δ.

This compound is known, see EP 221611.

PREPARATION 2

1-Cyclohexyl-2-diazoethanone (I)

A solution of diazomethane is prepared from N-methyl-N'-nitro-N-nitroso guanidine (12.5 g), potassium hydroxide (50%, 20 ml), and ether (300 ml). TEA (7.7 ml) is added to the diazomethane solution (65%) followed by cyclohexane carboxylic acid chloride (7.4 ml) slowly at 0°. The reaction is stirred at 0° for 1 hr then for 18 hrs at 22°. A porecipitate forms, it is filtered and washed with ether, and the filtrate concentrated. The resulting oil is cooled to −78°, triturated with ether, then warmed to 22° and concentrated with reduced pressure and heat to give the title compound as an oil, NMR (acetone-d$_6$) 5.4 and 1.4–0.8 δ.

PREPARATION 3

1-Diazo-3-[2-fluoro(1,1'-biphenyl)-4-yl]-butan-2-one (I)

Flurbiprofen (20.03 g) and thionyl chloride (21 ml) are refluxed for 16 hrs, then the excess thionyl chloride is removed under reduced pressure with heat. The residue is distilled to give the acid chloride which is used without further characterization.

Diazomethane is prepared as in PREPARATION 2 to give approximately 55 mmol. TEA (7.7 ml) is added to the diazomethane solution (300 ml) at −78° under nitrogen, followed by dropwise addition of the flurbiprofen acid chloride (14.4 g) in ether (50 ml). The reaction mixture is stirred for 15 min at −78° then 1 hr at −20°. The reaction is filtered, the filtrate washed with acetic acid (10%), water, saturated sodium bicarbonate solution and saline, then dried with sodium sulfate and concentrated under reduced pressure with heat to give the title compound as an oil, NMR (CDCl$_3$) 8.0–6.8, 5.1, 3.5 and 1.5 δ.

PREPARATION 4

1-Diazo-2-butanone (I)

The ethereal diazomethane solution [prepared by adding 12.5 g n-methyl-n-nitro-n-nitroso guanidine to potassium hydroxide (50%, 20 ml) and ether (200 ml) at 0°, stirring for 1 hr, and decanting the ether layer; 65% presumed yield] is treated with TEA 97.7 ml) at 0°, then dropwise with propionyl chloride (5.2 ml) in ether (25 ml). After stirring for 19 hrs, the reaction is filtered through celite and concentrated to give the title compound as an oil.

PREPARATION 5

2-Diazo-1-[4-nitrophenyl]-ethanone (II)

The ethereal diazomethane solution [prepared by adding 12.5 g n-methyl-n-nitro-n-nitroso guanidine to potassium hydroxide (50%, 20 ml) and ether (200 ml) at 0°, stirring for 1 hr, and decanting the ether layer; 65% presumed yield] is treated with TEA (7.7 ml) at 0°, then dropwise with p-nitrobenzoyl chloride (10.21 ml) in ether (25 ml). After stirring for 19 hrs, the reaction is filtered through celite and concentrated to give the title compound.

PREPARATION 6

2-Diazo-1-phenylethanone (I)

An ethereal solution of diazomethane is prepared from n-methyl-n-nitro-n-nitroso guanidine (15.72 g) for an estimated yield of 64 mmol. To the ethereal solution (400 ml) at 0° is added triethylamine (9.0 ml, 64 mmol), then dropwise benzoyl chloride (7.4 ml, 64 mmol). The reaction is warmed to 22° and stirred for 20 hrs, then filtered through celite and concentrated. The residue is recrystallized from ether/pentane to give the title compound.

PREPARATION 7

2-Diazo-1-phenylethanone (I)

Sodium hydride (50% in oil, 0.53 g) is suspended in ether (20 ml), cooled to 0°, then treated dropwise with a mixture of acetophenone 1.2 ml) and ethyl formate (0.90 ml). The reaction is stirred 1 hr at 0° then overnight at 22°. The precipitate is filtered and washed well with ether to give a solid. The solid is suspended in ethanol (10 ml), cooled to 0°, then treated dropwise with tosyl azide (0.97 g). The reaction is stirred for 3 hrs, concentrated, dissolved in 1N sodium hydroxide and extracted with ether. The ether is washed with water, dried with sodium sulfate and concentrated to give the title compound.

PREPARATION 8

2-Chloro-2-oximino-1-phenylethanone (I)

Phenacyl chloride (15.4 g) is dissolved in ether (100 ml) and hydrogen chloride gas is bubbled through the solution. Isoamyl nitrite (13.4 ml) is added in 0.5 to 1 ml portions over a 30 min period. Hydrochloric acid is continuously bubbled through the solution for an additional 15 min. The reaction is concentrated under reduced pressure to an oil, stored under vacuum in the presence of sulfuric acid, sodium hydroxice, and calcium chloride. The oil is crystallized from toluene and carbon tetrachloride to give the title compound.

EXAMPLE 1

[5-Benzoyl-2,4-dihydro-3H-pyrazol-3-ylidene]bisphosphonic acid tetraethyl ester (III)

Ethenylidene bisphosphonic acid tetraethyl ester (II, PREPARATION 1, 6.00 g) in ether (20 ml) is treated with solid 2-diazo-1-phenylethanone (2.92 g) and stirred at 22° for 20 hrs. The precipitate is collected and washed with ether to give the title compound. An analytical sample is obtained by recrystallization from methylene chloride/hexane, mp 133.5°–134°; MS (m/e) 446, 327, 309, 281, 271, 253, 243, 215, 175; IR (mineral oil mull) 3183, 1631, 1600, 1578, 1548, 1433, 1260, 1242, 1161, 1067, 1043, 1020, 1001, 995, 976 and 962 cm$^{-1}$; NMR (CDCl$_3$) 8.10, 7.50, 6.90, 4.27, 3.69 and 1.34 δ.

EXAMPLE 2

[5-Benzoyl-2,4-dihydro-3H-pyrazol-3-ylidene]bisphosphonic acid, disodium salt (III)

[5-Benzoyl-2,4-dihydro-3H-pyrazol-3-ylidene]bisphosphonic acid tetraethyl ester (III, EXAMPLE 1, 2.07 g) in chloroform (10 ml) is treated with bromotrimethylsilane (3.7 ml), heated to 40° for 5 hrs, and then concentrated under reduced pressure with heat. The residue is diluted with ethyl acetate and water, then stirred for 30 min. The layers are separated and the aqueous layer is treated with activated charcoal, filtered through celite, and freeze dried to give the free acid. The crude acid is then converted to the disodium salt. The acid (1.43 g) in methanol (15 ml) is warmed to dissolve most of the solid, filtered, then treated with a sodium methoxide in methanol solution (25%, 2.0 ml). The reaction mixture is cooled, filtered, and the precipitate air dried to give the title compound mp dec >170°; MS (m/e) 379, 357, 335, 315, 297, 281, 267, 253 and 239; RI (mineral oil mull) 3209, 1599, 1572, 1267, 1178, 1098, 1029, 1002 and 914 cm$^{-1}$; NMR (D$_2$O) 7.9–7.45 and 3.53 δ.

EXAMPLE 3

[5-(Cyclohexylcarbonyl)-2,4-dihydro-3H-pyrazol-3-ylidene]bisphosphonic acid tetraethyl ester (III)

1-Cyclohexyl-2-diazoethanone (I, PREPARATION 2, 3.1 g) and ethenylidene bisphosphonic acid tetraethyl ester (II, PREPARATION 1, 6.00 g) are stirred in ether (20 ml) for 24 hrs at 22°. The precipitate is filtered, washed with ether, then recrystallized from ethyl acetate to give the title compound, mp 166°–165°; MS (m/e) 452, 341, 315, 287, 259, 241, 223 and 205; IR (mineral oil mull) 3186, 1656, 1552, 1449, 1267, 1253, 1241, 1162, 1041, 1019, 995 and 969 cm$^{-1}$; NMR (CDCl$_3$) 6.77, 4.24, 3.45, 3.24 and 1.9–1.2 δ.

EXAMPLE 4

[5-(Cyclohexylcarbonyl)-2,4-dihydro-3H-pyrazol-3-ylidene]bisphosphonic acid dipotassium salt (III)

Following the general procedure of EXAMPLE 2 and making noncritical variations but starting with [5-(Cyclohexylcarbonyl)-2,4-dihydro-3H-pyrazol-3-ylidene]bisphosphonic acid tetraethyl ester (III, EXAMPLE 3, 2.08 g) and using potassium hydroxide in methanol, the title compound is obtained, mp dec >150°; MS (m/e) 495, 455, 417, 379 and 341; IR (mineral oil mull) 3177, 1630, 1547, 1350, 1166, 1138, 1076, 1058 and 972 cm$^{-1}$; NMR (CDCl$_3$, D$_2$O) 3.31, 3.11, 1.69 and 1.30 δ.

EXAMPLE 5

[5-[2-(2-Fluoro[1,1'-biphenyl]-4-yl)-1-oxopropyl]-2,4-dihydro-3H-pyrazol-3-ylidene]bisphosphonic acid tetraethyl ester (III)

Ethenylidene bisphosphonic acid tetraethyl ester (II, PREPARATION 1, 11.1 g) and 1-diazo-3-[2-fluoro(1,1'-biphenyl)-4-yl]-butan-2-one (I, PREPARATION 3, 10.0 g) are stirred for 18 hrs in ether (40 ml). A seed crystal from an earlier reaction is added to the mixture, whereupon the reaction sets up into a solid mass. The precipitate is filtered, then recrystallized from methylene chloride/hexane (45/55) to give the title compound, mp 109°–110°; MS (m/e) 568, 431, 403, 385, 341, 313, 301 and 199; IR (mineral oil mull) 3179, 1656, 1557, 1265, 1246, 1033, 1009, 993, 976 and 965 cm$^{-1}$; NMR (CDCl$_3$) 7.4, 7.2, 6.91, 4.81, 4.4, 4.05, 3.4, 1.49, 1.34, 1.16 and 1.08 δ; CMR (CDCl$_3$) 195.1, 162, 158, 149, 142, 136, 130.7, 128.8, 128.5, 127.6, 123.9, 115.8, 115.6, 64.3, 63.6, 46.1, 36.4, 17.7, 16.5, 16.2 and 16.1 δ.

EXAMPLE 6

[5-[2-(2-Fluoro[1,1'-biphenyl]-4-yl)-1-oxopropyl]-2,4-dihydro-3H-pyrazol-3-ylidene]bisphosphonic acid dipotassium salt with ethanol (III)

Following the general procedure of EXAMPLE 2 and making non-critical variations but starting with p5-[2-(2-fluoro[1,1'-biphenyl]-4-yl)-1-oxopropyl]-2,4-dihydro-3H-pyrazol-3-ylidene]bisphosphonic acid tetraethyl ester (III, EXAMPLE 5, 4.00 g) and using potassium hydroxide in ethanol, the title compound is obtained, mp dec>140°; MS (m/e) 533, 495, 451, 413 and 375; IR (mineral oil mull) 1651, 1623, 1581, 1561, 1483, 1219, 1074 and 1011 cm$^{-1}$; NMR (CDCl$_3$) 7.15, 3.68, 3.38, 1.35 and 1.20 δ.

EXAMPLE 7

[3-Methyl-5(4H)-isoxazolyidene]bisphosphonic acid tetraethyl ester (III)

Nitroethane (2.4 ml), TEA (6 drops) and toluene (9 ml) are added in one portion to a mixture of ethenylidene bisphosphonic acid tetraethyl ester (II, PREPARATION 1, 10.0 g) and phenyl isocyanate (6.6 ml) in toluene (16 ml). The mixture is stirred at 20°–25° for 30 min then at reflux for 4 hrs. The reaction is then cooled, filtered and the precipitate washed with ethyl acetate. The filtrate is concentrated under reduced pressure with heat. Column chromatography eluting with acetone/methylene chloride (1/1) gives the title compound, NMR (CDCl$_3$) 4.2, 3.5, 2.1 and 1.3 δ.

EXAMPLE 8

[3-Methyl-5(4H)-isoxazolylidene]bisphosphonic acid disodium salt (III)

[3-Methyl-5(4H)-isoxazolylidene]bisphosphonic acid tetraethyl ester (III, EXAMPLE 7, 3.00 g) is dissolved in chloroform (20 ml), treated with bromotrimethyl silane (6.6 ml) and heated to 40° for 4 hrs, then under reduced pressure with heat. The residue is taken up in ethyl acetate and water and stirred for 20 min. The aqueous layer is separated, washed with ethyl acetate, then freeze dried to give (3-methyl-5(4H)-isoxazolylidene)bisphosphonic acid (III).

The free acid, [3-methyl-5(4H)-isoxazolylidene]bisphosphonic acid (III, 1.756 g) is dissolved in methanol (20 ml), treated with Darco, and filtered through celite. The filtrate is treated with 25% sodium methoxide/methanol (25/75, 3.2 ml), stirred for 5 min, then filtered to give the title compound, mp dec>250°; MS (m/e) 290, 268, 246 and 211; IR (mineral oil mull) 3300, 2345, 1648, 1548, 1330, 1191, 1110 and 970 cm$^{-1}$; NMR (D$_2$O) 3.45 and 1.89 δ.

EXAMPLE 9

[3-Phenyl-5(4H)-isoxazolylidene]bisphosphonic acid tetraethyl ester (III)

Benzaldehyde-wyn-oxime (3.83 g) is dissolved in methylene chloride (30 ml), treated with a steady stream of chlorine gas for 5 min, then under reduced pressure with heat. The residue is again dissolved in methylene chloride (30 ml), treated with TEA (8.8 ml), and stirred for 5 min. Ethenylidene bisphosphonic acid tetraethyl ester (II, PREPARATION 1, 9.00 g) in methylene chloride (10 ml) is added and the reaction stirred well for 1 hr. The solution is then washed with hydrochloric acid (1N), saturated sodium bicarbonate and saline, dried with magnesium sulfate, and concentrated under reduced pressure with heat. Column chromatography eluting with hexane/acetone (7/3) and pooling the appropriate fraction gives the title compound as an oil, NMR (CDCl$_3$) 7.6, 7.3, 4.3, 3.9 aand 1.3 δ.

EXAMPLE 10

[3-Phenyl-5(4H)-isoxazolylidene]bisphosphonic acid PP'-diethyl ester disodium salt (III)

[3-Phenyl-5(4H)-isoxazolylidene]bisphosphonic acid tetraethyl ester (III, 9, 4.19 g) is dissolved in methyl ethyl ketone (10 ml) and heated to reflux with sodium iodide (3.00 g) for 4 hrs. Filtered, resuspended in methanol and filtered again to give the title compound, MS (m/e) 408, 386, 362, 327 and 298; IR (mineral oil mull) 3415, 1679, 1601, 1572, 1366, 1223, 1204, 1124, 1081, 1076 and 1051 cm$^{-1}$; NMR (CDCl$_3$) δ; NMR (CDCl$_3$) 7.7, 7.4, 4.4, 4.0 and 1.3 δ.

EXAMPLE 11

[3-Phenyl-5(4H)-isoxazolylidene]bisphosphonic acid monopotassium salt (III)

The diphosphonate, [3-phenyl-5(4H)-isoxazolylidene]bisphosphonic acid tetraethyl ester (III, EXAMPLE 9, 2.10 g) in chloroform (10 ml) is treated with bromotrimethylsilane (4.0 ml) and heated to 50°-60° for 5 hrs. The reaction is concentrated under reduced pressure with heat, taken up in ethyl acetate, extracted with water, and the aqueous fractions are filtered and freeze dried to give (3-phenyl-5(4H)isoxazolylidene)bisphosphonic acid.

The free acid, [3-phenyl-5(4H)-isoxazolylidene]bisphosphonic acid, is then dissolved in ethanol (15 ml), treated with a solution of potassium hydroxide (560 mg, 10 mmol) in ethanol (10 ml), the precipitate collected and washed with ether to give the title compound, mp dec>250°; MS (m/e) 422, 384, 346 and 308; IR (mineral oil mull) 3054, 3029, 2317, 1609, 1572, 1497, 1206 and 1068 cm$^{-1}$; NMR (D$_2$O) 3.94 δ.

EXAMPLE 12

[2,4-Dihydro-5-(1-oxopropyl)-3H-pyrazol-3-ylidene]-bisphosphonic acid tetraethyl ester (III)

1-Diazo-2-butanone (I, PREPARATION 4, 3.1 g) in ether (50 ml) is treated with ethenylidene bisphosphonic acid tetraethyl ester (II, PREPARATION 1, 9.5 g), stirred at 20°-25° overnight, and concentrated. The concentrate is crystallized twice from methylene chloride/SSB to give the title compound, mp 96°-98°; MS (m/e) 398, 261, 233 and 205; IR (mineral oil mull) 3210, 0664, 1265, 1245, 1046, 1024, 997 and 983 cm$^{-1}$; NMR (CDCl$_3$) 6.92, 4.14–4.33, 3.48, 2.82, 1.30–1.36 and 1.12 δ; CMR (CDCl$_3$) 196, 149, 66, 64, 36, 31, 16 and 8 δ.

EXAMPLE 13

[2,4-Dihydro-5-(1-oxopropyl)-3H-pyrazol-3-ylidene]-bisphosphonic acid (III)

[2,4-Dihydro-5-(1-oxopropyl)-3H-pyrazol-3-ylidene]-bisphosphonic acid tetraethyl ester (III, EXAMPLE 12, 1.56 g) and bromotrimethylsilane (2.6 ml) in chloroform (20 ml) are stirred at 50° for 4 hrs, then concentrated. The concentrate is diluted with water and ethyl acetate, shaken, and the aqueous layer separated and freeze dried to give the title compound, mp 148° foamed, IR (mineral oil mull) 3325, 1597, 1532, 1430, 1189, 1173, 1060, 1019 and 937 cm$^{-1}$; NMR (D$_2$O) 3.40, 2.84 and 1.07 δ.

EXAMPLE 14

[2,4-Dihydro-5-(nitrobenzoyl)-3H-pyrazol-3-ylidene]-bisphosphonic acid tetraethyl ester (III)

2-Diazo-1-[4-nitrophenyl]-ethanone (I, PREPARATION 5, 2.7 g) in ether (30 ml) is treated with ethenylidene bisphosphonic acid tetraethyl ester (II, PREPARATION 1, 4.6 g) stirred at 20°-25° for 48 hrs, filtered and the solid washed with ether. The solid is crystallized twice from methylene chloride/SSB to give the title compound, mp 111°-112°; IR (mineral oil mull) 3185, 1635, 1555, 1515, 1353, 1253, 1237, 1056, 1042, 1017, 994 and 603 cm$^{-1}$; CMR (CDCl$_3$) 185, 150, 148, 141, 130, 123, 65, 64, 37 and 16 δ.

EXAMPLE 15

[2,4-Dihydro-5-(4-nitrobenzoyl)-3H-pyrazol-3-ylidene]-bisphosphonic acid (III)

Following the general procedure of EXAMPLE 13 and making noncritical variation but starting with [2,4-dihydro-5-(4-nitrobenzoyl)-3H-pyrazol-3-ylidene]bisphosphonic acid tetraethyl ester (III, EXAMPLE 14, 2.4 g) the title compound is obtained, mp 180° dec; NMR (CDCl$_3$) 8.23, 7.98 and 3.64 δ; CMR (D$_2$O) 188, 149, 145, 142, 130, 123, 68 and 35 δ.

EXAMPLE 16

[3-Benzoyl-5(4H)isoxazolylidene]bisphosphonic acid tetraethyl ester (III)

A solution of 2-chloro-2-oximino-1-phenylethanone (I, PREPARATION 8, 0.92 g) and ethenylidene bisphosphonic acid tetraethyl ester (II, PREPARATION 1, 1.50 g) in methylene chloride (5 ml) are treated with triethylamine (1.0 ml) and stirred for 20 hrs. The reaction is diluted with ethyl acetate, washed with water, hydrochloric acid (1N) and saturated sodium bicarbonate, dried with magnesium sulfate and concentrated under reduced pressure. Two reactions of identical size are chromatographed over a silica gel column eluting with ethyl acetate. The appropriate fractions are pooled and concentrated to give the title compound, NMR (CDCl$_3$) 8.11, 8.54, 7.40, 4.23, 3.90 and 1.28 δ.

EXAMPLES 17-25

Following the general procedure of EXAMPLES 1 and 3 and making non-critical variations but starting with the nitrogen containing dipoles (I) 17A, 18A, . . . 25A, the corresponding unsaturated geminal phosphonates (III) of EXAMPLES 17B, 18B, . . . 25B, are obtained.

The nitrogen containing dipoles (I)
17A 1-(4'-chlorophenyl)-2-diazoethanone
18A 1-(2',4'-dichlorophenyl)-2-diazoethanone
19A 1-diazo-3,3-dimethylbutanone
20A 1-(2'-fluorophenyl)-2-diazoethanone
21A 1-(4'-methoxyphenyl)-2-diazoethanone
22A 1-(4'-methylphenyl)-2-diazoethanone
23A 1-(3'-methylphenyl)-2-diazoethanone
24A 1-(3'-fluorophenyl)-2-diazoethanone
25A 1-(2'-methylphenyl)-2-diazoethanone produce the unsaturated geminal phosphonates (III)
17B [5-(4'-chlorobenzoyl)-2,4-dihydro-3H-pyrazol-3-ylidene]bisphosphonic acid tetraethyl ester, mp 101°-102°.
18B [5-(2',4'-dichlorobenzoyl)-2,4-dihydro-3H-pyrazol-3-ylidene]-bisphosphonic acid tetraethyl ester, mp 155°-156°.
19B [5-(2,2-dimethyl-1-oxopropyl)-2,4-dihydro-3H-pyrazol-3-ylidene]-bisphosphonic acid tetraethyl ester, mp 106°-107°.
20B [5-(2'-fluorobenzoyl)-2,4-dihydro-3H-pyrazol-3-ylidene]-bisphosphonic acid tetraethyl ester, mp 185°-186°.
21B [5-(4'-methoxybenzoyl)-2,4-dihydro-3H-pyrazol-3-ylidene]-bisphosphonic acid tetraethyl ester, mp 115°-116°.
22B [5-(4'-methylbenzoyl)-2,4-dihydro-3H-pyrazol-3-ylidene]-bisphosphonic acid tetraethyl ester, mp 116°-117°.
23B [5-(3'-methylbenzoyl)-2,4-dihydro-3H-pyrazol-3-ylidene]-bisphosphonic acid tetraethyl ester, mp 91°-92°.
24B [5-(3'-fluorobenzoyl)-2,4-dihydro-3H-pyrazol-3-ylidene]bisphosphonic acid tetraethyl ester, mp 104°-105°.
25B [5-(2'-methylbenzoyl)-2,4-dihydro-3H-pyrazol-3-ylidene]bisphosphonic acid tetraethyl ester, mp 162°-163°.

EXAMPLES 26-81

Following the general procedure of EXAMPLES 1 and 3 and making non-critical variations but starting with the nitrogen containing dipoles (I) 26A, . . . 81A, the corresponding unsaturated geminal phosphonates (III) of EXAMPLES 26B, . . . 81B are obtained.

The nitrogen containing dipoles (I) 26A, . . . 81A are prepared following the general procedure of PREPARATIONS 5 or 6.
26A 1-(2'-bromophenyl)-2-diazoethanone
27A 1-(3'-bromophenyl)-2-diazoethanone
28A 1-(4'-bromophenyl)-2-diazoethanone
29A 1-(2'-chlorophenyl)-2-diazoethanone
30A 1-(3'-chlorophenyl)-2-diazoethanone
31A 1-(3',4'-dichlorophenyl)-2-diazoethanone
32A 1-(3',5'-dichlorophenyl)-2-diazoethanone
33A 1-(2',6'-dichlorophenyl)-2-diazoethanone
34A 1-(2',3'4'-trichlorophenyl)-2-diazoethanone
35A 1-(4'-fluorophenyl)-2-diazoethanone
36A 1-(2',3',4',5',6'-pentafluorophenyl)-2-diazoethanone
37A 1-(2'-methoxyphenyl)-2-diazoethanone
38A 1-(3'-methoxyphenyl)-2-diazoethanone
39A 1-(2',4'-dimethoxyphenyl)-2-diazoethanone
40A 1-(3',5'-dimethoxyphenyl)-2-diazoethanone
41A 1-(2'-chloro-4'-methoxyphenyl)-2-diazoethanone
42A 1-(4'-chloro-2'-methoxyphenyl)-2-diazoethanone
43A 1-(3'-chloro-4'-methoxyphenyl)-2-diazoethanone
44A 1-(4'-chloro-3'-methoxyphenyl)-2-diazoethanone
45A 1-(2'-ethoxyphenyl)-2-diazoethanone
46A 1-(3'-ethoxyphenyl)-2-diazoethanone
47A 1-(4'-ethoxyphenyl)-2-diazoethanone
48A 1-(2'-phenoxyphenyl)-2-diazoethanone
49A 1-(3'-phenoxyphenyl)-2-diazoethanone
50A 1-(4'-phenoxyphenyl)-2-diazoethanone
51A 1-(2'-methylthiophenyl)-2-diazoethanone
52A 1-(3'-methylthiophenyl)-2-diazoethanone
53A 1-(4'-methylthiophenyl)-2-diazoethanone
54A 1-(2'-chloro-4'-methylphenyl)-2-diazoethanone
55A 1-(4'-chloro-2'-methylphenyl)-2-diazoethanone
56A 1-(3'-chloro-4'-methylphenyl)-2-diazoethanone
57A 1-(4'-chloro-3'-methylphenyl)-2-diazoethanone
58A 1-(2'-ethylphenyl)-2-diazoethanone
59A 1-(3'-ethylphenyl)-2-diazoethanone
60A 1-(4'-ethylphenyl)-2-diazoethanone
61A 1-(4'-tert butylphenyl)-2-diazoethanone
62A 1-(2',4'-dimethylphenyl)-2-diazoethanone
63A 1-(3',5'-dimethylphenyl)-2-diazoethanone
64A 1-(2'-phenylphenyl)-2-diazoethanone
65A 1-(3'-phenylphenyl)-2-diazoethanone
66A 1-(4'-phenylphenyl)-2-diazoethanone
67A 1-(4'-inophenyl)-2-diazoethanone
68A 1-(4'-dimethylaminophenyl)-2-diazoethanone
69A 1-(4'-diethylaminophenyl)-2-diazoethanone
70A 1-(3'-trifluoromethylphenyl)-2-diazoethanone
71A 1-(1'-naphthoyl)-2-diazoethanone
72A 1-(2'-naphthoyl)-2-diazoethanone
73A 1-(6'-quinolinoyl)-2-diazoethanone
74A 1-(8'-quinolinoyl)-2-diazoethanone
75A 1-(2'-thienylcarbonyl)-2-diazoethanone
76A 1-(2'-pyridylcarbonyl)-2-diazoethanone
77A 1-(nicotinoyl)-2-diazoethanone
78A 1-(4-pyridylcarbonyl)-2-diazoethanone
79A 1-(cyclopropanoyl)-2-diazoethanone
80A 1-(cyclobutanoyl)-2-diazoethanone
81A 1-(cyclopentanoyl)-2-diazoethanone
82A 1-(9'-anthraconyl)-2-diazoethanone
83A 1-(3',5'-difluorophenyl)-2-diazoethanone produce the unsaturated geminal phosphonates (III)
26B [5-(2'-bromobenzoyl)-2,4-dihydro-3H-pyrazol-3-ylidene]bisphosphonic acid tetraethyl ester
27B [5-(3'-bromobenzoyl)-2,4dihydro-3H-pyrazol-3-ylidene]bisphosphonic acid tetraethyl ester
28B [5-(4'-bromobenzoyl)-2,4-dihydro-3H-pyrazol-3-ylidene]bisphosphonic acid tetraethyl ester, mp 104°-105°
29B [5-(2'-chlorobenzoyl)-2,4-dihydro-3H-pyrazol-3-ylidene]bisphosphonic acid tetraethyl ester
30B [5-(3'-chlorobenzoyl)-2,4-dihydro-3H-pyrazol-3-ylidene]bisphosphonic acid tetraethyl ester
31B [5-(3',4'-dichlorobenzoyl)-2,4-dihydro-3H-pyrazol-3-ylidene]bisphosphonic acid tetraethyl ester
32B [5-(3',5'-dichlorobenzoyl)-2,4-dihydro-3H-pyrazol-3-ylidene]bisphosphonic acid tetraethyl ester 33B [5-(2',6'-dichlorobenzoyl)-2,4-dihydro-3H-pyrazol-3-ylidene]bisphosphonic acid tetraethyl ester
34B [5-(2',3',4'-trichlorobenzoyl)-2,4-dihydro-3H-pyrazol-3-ylidene]bisphosphonic acid tetraethyl ester, mp 171°–172°.
35B [5-(4'-fluorobenzoyl)-2,4-dihydro-3H-pyrazol-3-ylidene]bisphosphonic acid tetraethyl ester
36B [5-(2',3',4',5',6'-pentafluorobenzoyl)-2,4-dihydro-3H-pyrazol-3-ylidene]bisphosphonic acid tetraethyl ester
37B [5-(2'-methoxybenzoyl)-2,4-dihydro-3H-pyrazol-3-ylidene]bisphosphonic acid tetraethyl ester
38B [5-(3'-methoxybenzoyl)-2,4-dihydro-3H-pyrazol-3-ylidene]bisphosphonic acid tetraethyl ester, mp 90°–91°
39B [5-(2',4'-dimethoxybenzoyl)-2,4-dihydro-3H-pyrazol-3-ylidene]bisphosphonic acid tetraethyl ester, mp 120°
40B [5-(3',5'-dimethoxybenzoyl)-2,4-dihydro-3H-pyrazol-3-ylidene]bisphosphonic acid tetraethyl ester
41B [5-(2'-chloro-4'-methoxybenzoyl)-2,4-dihydro-3H-pyrazol-3-ylidene]bisphosphonic acid tetraethyl ester
42B [5-(4'-chloro-2'-methoxybenzoyl)-2,4-dihydro-3H-pyrazol-3-ylidene]bisphosphonic acid tetraethyl ester
43B [5-(3'-chloro-4'-methoxybenzoyl)-2,4-dihydro-3H-pyrazol-3-ylidene]bisphosphonic acid tetraethyl ester
44B [5-(4'-chloro-3'-methoxybenzoyl)-2,4-dihydro-3H-pyrazol-3-ylidene]bisphosphonic acid tetraethyl ester
45B [5-(2'-ethoxybenzoyl)-2,4-dihydro-3H-pyrazol-3-ylidene]bisphosphonic acid tetraethyl ester
46B [5-(3'-ethoxybenzoyl)-2,4-dihydro-3H-pyrazol-3-ylidene]bisphosphonic acid tetraethyl ester
47B [5-(4'-ethoxybenzoyl)-2,4-dihydro-3H-pyrazol-3-ylidene]bisphosphonic acid tetraethyl ester
48B [5-(2'-phenoxybenzoyl)-2,4-dihydro-3H-pyrazol-3-ylidene]bisphosphonic acid tetraethyl ester
49B [5-(3'-phenoxybenzoyl)-2,4-dihydro-3H-pyrazol-3-ylidene]bisphosphonic acid tetraethyl ester
50B [5-(4'-phenoxybenzoyl)-2,4-dihydro-3H-pyrazol-3-ylidene]bisphosphonic acid tetraethyl ester
51B [5-(2'-methylthiobenzoyl)-2,4-dihydro-3H-pyrazol-3-ylidene]bisphosphonic acid tetraethyl ester
52B [5-(3'-methylthiobenzoyl)-2,4-dihydro-3H-pyrazol-3-ylidene]bisphosphonic acid tetraethyl ester
53B [5-(4'-methylthiobenzoyl)-2,4-dihydro-3H-pyrazol-3-ylidene]bisphosphonic acid tetraethyl ester
54B [5-(2'-chloro-4'-methylbenzoyl)-2,4-dihydro-3H-pyrazol-3-ylidene]bisphosphonic acid tetraethyl ester
55B [5-(4'-chloro-2'-methylbenzoyl)-2,4-dihydro-3H-pyrazol-3-ylidene]bisphosphonic acid tetraethyl ester
56B [5-(3'-chloro-4'-methylbenzoyl)-2,4-dihydro-3H-pyrazol-3-ylidene]bisphosphonic acid tetraethyl ester
57B [5-(4'-chloro-3'-methylbenzoyl)-2,4-dihydro-3H-pyrazol-3-ylidene]bisphosphonic acid tetraethyl ester
58B [5-(2'-ethylbenzoyl)-2,4-dihydro-3H-pyrazol-3-ylidene]bisphosphonic acid tetraethyl ester
59B [5-(3'-ethylbenzoyl)-2,4-dihydro-3H-pyrazol-3-ylidene]bisphosphonic acid tetraethyl ester
60B [5-(4'-ethylbenzoyl)-2,4-dihydro-3H-pyrazol-3-ylidene]bisphosphonic acid tetraethyl ester
61B [5-(4'-tert-butylbenzoyl)-2,4-dihydro-3H-pyrazol-3-ylidene]bisphosphonic acid tetraethyl ester
62B [5-(2',4'-dimethylbenzoyl)-2,4-dihydro-3H-pyrazol-3-ylidene]bisphosphonic acid tetraethyl ester
63B [5-(3',5'-dimethylbenzoyl)-2,4-dihydro-3H-pyrazol-3-ylidene]bisphosphonic acid tetraethyl ester
64B [5-(2'-phenylbenzoyl)-2,4-dihydro-3H-pyrazol-3-ylidene]bisphosphonic acid tetraethyl ester
65B [5-(3'-phenylbenzoyl)-2,4-dihydro-3H-pyrazol-3-ylidene]bisphosphonic acid tetraethyl ester
66B [5-(4'-phenylbenzoyl)-2,4-dihydro-3H-pyrazol-3-ylidene]bisphosphonic acid tetraethyl ester
67B [5-(4'-morpholinobenzoyl)-2,4-dihydro-3H-pyrazol-3-ylidene]bisphosphonic acid tetraethyl ester
68B [5-(4'-dimethylaminobenzoyl)-2,4-dihydro-3H-pyrazol-3-ylidene]bisphosphonic acid tetraethyl ester
69B [5-(4'-diethylaminobenzoyl)-2,4-dihydro-3H-pyrazol-3-ylidene]bisphosphonic acid tetraethyl ester
70B [5-(4'-trifluoromethylbenzoyl)-2,4-dihydro-3H-pyrazol-3-ylidene]bisphosphonic acid tetraethyl ester, mp 94°–95°
71B [5-(1'-naphthoyl)-2,4-dihydro-3H-pyrazol-3-ylidene]bisphosphonic acid tetraethyl ester, mp 176°–177°
72B [5-(2'-naphthoyl)-2,4-dihydro-3H-pyrazol-3-ylidene]bisphosphonic acid tetraethyl ester
73B [5-(6'-quinolinoyl)-2,4-dihydro-3H-pyrazol-3-ylidene]bisphosphonic acid tetraethyl ester
74B [5-(8'-quinolinoyl)-2,4-dihydro-3H-pyrazol-3-ylidene]bisphosphonic acid tetraethyl ester
75B [5-(2'-thienylcarbonyl)-2,4-dihydro-3H-pyrazol-3-ylidene]bisphosphonic acid tetraethyl ester
76B [5-(2'-pyridylcarbonyl)-2,4-dihydro-3H-pyrazol-3-ylidene]bisphosphonic acid tetraethyl ester
77B [5-(nicotinoyl)-2,4-dihydro-3H-pyrazol-3-ylidene]bisphosphonic acid tetraethyl ester
78B [5-(4'-pyridylcarbonyl)-2,4-dihydro-3H-pyrazol-3-ylidene]bisphosphonic acid tetraethyl ester
79B [5-(cyclopropanoyl)-2,4-dihydro-3H-pyrazol-3-ylidene]bisphosphonic acid tetraethyl ester, mp 133°–134°
80B [5-(cyclobutanoyl)-2,4-dihydro-3H-pyrazol-3-ylidene]bisphosphonic acid tetraethyl ester
81B [5-(cyclopentanoyl)-2,4-dihydro-3H-pyrazol-3-ylidene]bisphosphonic acid tetraethyl ester
82B [5-(9-'anthracenoyl)-2,4-dihydro-3H-pyrazol-3-ylidene]bisphosphonic acid tetraethyl ester, mp 201°–202°
83B [5-(3',5'-difluorobenzoyl)-2,4-dihydro-3H-pyrazol-3-ylidene]bisphosphonic acid tetraethyl ester, 105°–106°.

CHART A

(I)

+

(II)

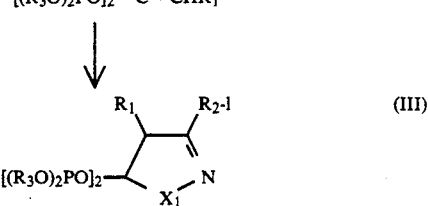

(III)

We claim:
1. An unsaturated geminal phosphate of formula (III)

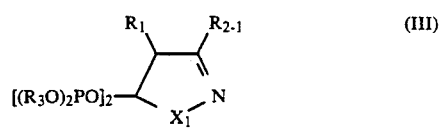

(III)

where
- $X_1$ is —O—, —NH— or —N—metal where metal is sodium, potassium, calcium, magnesium, copper, zinc, barium, silver or gold;
- $R_1$ is —H, $C_1$-$C_4$ alkyl, $C_3$-$C_7$ cycloalkyl, -$\phi$ optionally substituted with 1 through 5 —F, —Cl, —Br, —I, —$CF_3$, $C_1$-$C_6$ alkyl, $C_1$-$C_6$ cycloalkyl, $C_1$-$C_4$ alkoxy or $C_1$-$C_4$ alkylthio;
- $R_{2-1}$ is
  - $C_1$-$C_6$ alkyl,
  - $C_3$-$C_7$ cycloalkyl,
  - -$\phi$ optionally substituted with 1 through 5 —F, —Cl, —Br, —I, —$NO_2$, —CN, —$CF_3$, $C_1$-$C_6$ alkyl, $C_3$-$C_7$ cycloalkyl, $C_1$-$C_4$ alkoxy, $C_1$-$C_4$ alkylthio,
  - —CH(OH)—$R_{2-5}$ where $R_{2-5}$ is
    - (A) $C_1$-$C_{10}$ alkyl,
    - (B) $C_3$-$C_7$ cycloalkyl,
    - (C) -$\phi$ optionally substituted with 1 or 2 -$\phi$ or 1 through 5 —F, —Cl, —Br, —I, —$NO_2$, —CN, —$CF_3$, $C_1$-$C_6$ alkyl, $C_3$-$C_7$ cycloalkyl, $C_1$-$C_4$ alkoxy, $C_1$-$C_4$ alkylthio,
    - (D) 2- or 3-furanyl optionally substituted with 1 through 3 —F, —Cl, —Br, —I, —$NO_2$, —CN, —$CF_3$, $C_1$-$C_6$ alkyl, $C_3$-$C_7$ cycloalkyl, $C_1$-$C_4$ alkoxy, —O-$\phi$, $C_1$-$C_4$ alkylthio,
    - (E) 2-, 4- or 5-pyrimidyl optionally substituted with 1 through 3 —F, —Cl, —Br, —I, —$NO_2$, —CN, —$CF_3$, $C_1$-$C_6$ alkyl, $C_3$-$C_7$ cycloalkyl, $C_1$-$C_4$ alkoxy, $C_1$-$C_4$ alkylthio,
    - (F) 2-, 3- or 4-pyridinyl optionally substituted with 1 through 4 —F, —Cl, —Br, —I, —$NO_2$, —CN, —$CF_3$, $C_1$-$C_6$ alkyl, $C_3$-$C_7$ cycloalkyl, $C_1$-$C_4$ alkoxy, $C_1$-$C_4$ alkylthio,
    - (G) 2- or 3-thiophene optionally substituted with 1 through 3 —F, —Cl, —Br, —I, —$NO_2$, —CN, —$CF_3$, $C_1$-$C_6$ alkyl, $C_3$-$C_7$ cycloalkyl, $C_1$-$C_4$ alkoxy, $C_1$-$C_4$ alkylthio,
    - (H) 1- or 2-naphthalene optionally substituted with 1 through 7 —F, —Cl, —Br, —I, —$NO_2$, —CN, —$CF_3$, $C_1$-$C_6$ alkyl, $C_3$-$C_7$ cycloalkyl, $C_1$-$C_4$ alkoxy, $C_1$-$C_4$ alkylthio,
    - (I) 2-, 3-, 4-, 6-, 7- or 8-quinoline,
    - (J) 1-, 3-, 4-, 6-, 7- or 8-isoquinoline,
    - (K) 2-, 3-, 4-, 5-, 6- or 7-benzothiophene,
    - (L) 2-, 3-, 4-, 5-, 6- or 7-benzofuran,
    - (M) —$NR_{2-6}R_{2-7}$ where $R_{2-6}$ and $R_{2-7}$ are the same or different and are $C_1$-$C_4$ alkyl, -$\phi$,
      - —CO—$R_{2-8}$ wherein $R_{2-8}$ is $C_1$-$C_4$ alkyl or -$\phi$ optionally substituted with 1 -$CH_3$,
      - —$SO_2$—$R_{2-8}$ where $R_{2-8}$ is as defined above or where $R_{2-6}$ and $R_{2-7}$ are taken together with the attached nitrogen atom to form a ring selected from the group consisting of pyrrolidinyl, piperidinyl or morpholin-4-yl;
  - —CO—$R_{2-5}$ where $R_{2-5}$ is as defined above;
- $R_3$ is —H, $C_1$-$C_6$ alkyl, -$\phi$ or pharmaceutically acceptable salts thereof.

2. An unsaturated geminal phosphonate (III) according to claim 1 where $X_1$ is —NH—.

3. An unsaturated geminal phosphonate (III) according to claim 1 where $R_1$ is -H.

4. An unsaturated geminal phosphonate (III) according to claim 1 where $R_{2-1}$ is —CO—$R_{2-5}$ or —CH(OH)—$R_{2-5}$.

5. An unsaturated geminal phosphonate (III) according to claim 1 where $R_{2-1}$ is —CO-$\phi$ optionally substituted with —F, —Cl, —Br, —I, —CN, —$CF_3$, $C_1$-$C_4$ alkoxy, $C_1$-$C_4$ alkyl or cyclopropyl.

6. An unsaturated geminal phosphonate (III) according to claim 1 where $R_3$ is —H, sodium, potassium, calcium, magnesium, manganese, copper, gold, ethanolamine, diethanolamine, triethanolamine, zinc or 7. An unsaturated geminal phosphonate (III) according to claim 1 where $R_3$ is $C_1$-$C_4$ alkyl.

8. An unsaturated geminal phosphonate (III) according to claim 1 which is
- [5-benzoyl-2,4-dihydro-3H-pyrazol-3-ylidene]bisphosphonic acid tetraethyl ester,
- [5-(cyclohexylcarbonyl)-2,4-dihydro-3H-pyrazol-3-ylidene]bisphosphonic acid tetraethyl ester,
- [5-[2-(2-fluoro[1,1'-biphenyl]-4-yl)-1-oxopropyl]-2,4-dihydro-3H-pyrazol-3-ylidene]bisphosphonic acid tetraethyl ester,
- [3-methyl-5(4H)-isoxazolylidene]bisphosphonic acid tetraethyl ester,
- [3-phenyl-5(4H)-isoxazolylidene]bisphosphonic acid tetraethyl ester,
- [2,4-dihydro-5-(1-oxopropyl)-3H-pyrazol-3-ylidene]bisphosphonic acid tetraethyl ester,
- [2,4-dihydro-5-(4-nitrobenzoyl)-3H-pyrazol-3-ylidene]bisphosphonic acid tetraethyl ester,
- [3-benzoyl-5-(4H)-isoxazolylidene]bisphosphonic acid tetraethyl ester,
- [5-(4'-chlorobenzoyl)-2,4-dihydro-3H-pyrazol-3-ylidene]bisphosphonic acid tetraethyl ester,
- [5-(2',4'-dichlorobenzoyl)-2,4-dihydro-3H-pyrazol-3-ylidene]bisphosphonic acid tetraethyl ester,
- [5-(2,2-dimethyl-1-oxopropyl)-2,4-dihydro-3H-pyrazol-3-ylidene]bisphosphonic acid tetraethyl ester,
- [5-(2'-fluorobenzoyl)-2,4-dihydro-3H-pyrazol-3-ylidene]bisphosphonic acid tetraethyl ester,
- [5-(4'-methoxybenzoyl)-2,4-dihydro-3H-pyrazol-3-ylidene]bisphosphonic acid tetraethyl ester,
- [5-(4'-methylbenzoyl)-2,4-dihydro-3H-pyrazol-3-ylidene]bisphosphonic acid tetraethyl ester,
- [5-(3'-methylbenzoyl)-2,4-dihydro-3H-pyrazol-3-ylidene]bisphosphonic acid tetraethyl ester,
- [5-(3'-fluorobenzoyl)-2,4-dihydro-3H-pyrazol-3-ylidene]bisphosphonic acid tetraethyl ester,
- [5-(2'-methylbenzoyl)-2,4-dihydro-3H-pyrazol-3-ylidene]bisphosphonic acid tetraethyl ester,
- [5-(4'-bromobenzoyl)-2,4-dihydro-3H-pyrazol-3-ylidene]-bisphosphonic acid tetraethyl ester,
- [5-(2',3',4'-trichlorobenzoyl)-2,4-dihydro-3H-pyrazol-3-ylidene]bisphosphonic acid tetraethyl ester,
- [5-(3'-methoxybenzoyl)-2,4-dihydro-3H-pyrazol-3-ylidene]-bisphosphonic acid tetraethyl ester,
- [5-(2',4'-dimethoxybenzoyl)-2,4-dihydro-3H-pyrazol-3-ylidene]-bisphosphonic acid tetraethyl ester,
- [5-(3'-trifluoromethylbenzoyl)-2,4-dihydro-3H-pyrazol-3-ylidene]bisphosphonic acid tetraethyl ester,
- [5-(cyclopropanoyl)-2,4-dihydro-3H-pyrazol-3-ylidene]bisphosphonic acid tetraethyl ester,
- [5-(9-'anthracenoyl)-2,4-dihydro-3H-pyrazol-3-ylidene]bisphosphonic acid tetraethyl ester,
- [5-(3',5'-difluorobenzoyl)-2,4-dihydro-3H-pyrazol-3-ylidene]bisphosphonic acid tetraethyl ester.

9. An unsaturated geminal phosphonate (III) according to claim 1 which is
- [5-benzoyl-2,4-dihydro-3H-pyrazol-3-ylidene]bisphosphonic acid tetraethyl ester,

[5-(cyclohexylcarbonyl-2,4-dihydro-3H-pyrazol-3-ylidene]bisphosphonic acid tetraethyl ester,
[5-[2-(2-fluoro[1,1'-biphenyl]-4-yl)-1-oxopropyl]-2,4-dihydro-3H-pyrazol-3-ylidene]bisphosphonic acid tetraethyl ester,
[3-methyl-5(4H)-isoxazolylidene]bisphosphonic acid tetraethyl ester,
[3-phenyl-5(4H)-isoxazolylidene]bisphosphonic acid tetraethyl ester,
[2,4-dihydro-5-(4-nitrobenzoyl)-3H-pyrazol-3-ylidene]bisphosphonic acid tetraethyl ester,
[3-benzoyl-5(4H)-isoxazolylidene]bisphosphonic acid tetraethyl ester,
[5-(4'-chlorobenzoyl)-2,4-dihydro-3H-pyrazol-3-ylidene]bisphosphonic acid tetraethyl ester,
[5-(2',4'-dichlorobenzoyl)-2,4-dihydro-3H-pyrazol-3-ylidene]bisphosphonic acid tetraethyl ester,
[5-(2',2'-dimethyl-1-oxopropyl)-2,4-dihydro-3H-pyrazol-3-ylidene]bisphosphonic acid tetraethyl ester,
[5-(2'-fluorobenzoyl)-2,4-dihydro-3H-pyrazol-3-ylidene]bisphosphonic acid tetraethyl ester,
[5-(4'-methoxybenzoyl)-2,4-dihydro-3H-pyrazol-3-ylidene]bisphosphonic acid tetraethyl ester,
[5-(4'-methylbenzoyl)-2,4-dihydro-3H-pyrazol-3-ylidene]bisphosphonic acid tetraethyl ester,
[5-(3'-methylbenzoyl)-2,4-dihydro-3H-pyrazol-3-ylidene]bisphosphonic acid tetraethyl ester,
[5-(3'-fluorobenzoyl)-2,4-dihydro-3H-pyrazol-3-ylidene]bisphosphonic acid tetraethyl ester,
[5-(2'-methylbenzoyl)-2,4-dihydro-3H-pyrazol-3-ylidene]bisphosphonic acid tetraethyl ester,
[5-(4'-bromobenzoyl)-2,4-dihydro-3H-pyrazol-3-ylidene]-bisphosphonic acid tetraethyl ester,
[5-(2',3',4'-trichlorobenzoyl)-2,4-dihydro-3H-pyrazol-3-ylidene]bisphosphonic acid tetraethyl ester,
[5-(3'-methoxybenzoyl)-2,4-dihydro-3H-pyrazol-3-ylidene]bisphosphonic acid tetraethyl ester,
[5-(2',4'-dimethoxybenzoyl)-2,4-dihydro-3H-pyrazol-3-ylidene]bisphosphonic acid tetraethyl ester,
[5-(3'-trifluoromethylbenzoyl)-2,4-dihydro-3H-pyrazol-3-ylidene]bisphosphonic acid tetraethyl ester,
[5-(cyclopropanoyl)-2,4-dihydro-3H-pyrazol-3-ylidene]bisphosphonic acid tetraethyl ester,
[5-(9-'anthracenoyl)-2,4-dihydro-3H-pyrazol-3-ylidene]bisphosphonic acid tetraethyl ester,
[5-(3',5'-difluorobenzoyl)-2,4-dihydro-3H-pyrazol-3-ylidene]bisphosphonic acid tetraethyl ester.

10. An unsaturated geminal phosphonate (III) according to claim 1 which is
[5-(2'-bromobenzoyl)-2,4-dihydro-3H-pyrazol-3-ylidene]bisphosphonic acid tetraethyl ester,
[5-(3'-bromobenzoyl)-2,4-dihydro-3H-pyrazol-3-ylidene]bisphosphonic acid tetraethyl ester,
[5-(2'-chlorobenzoyl)-2,4-dihydro-3H-pyrazol-3-ylidene]bisphosphonic acid tetraethyl ester,
[5-(3'-chlorobenzoyl)-2,4-dihydro-3H-pyrazol-3-ylidene]bisphosphonic acid tetraethyl ester,
[5-(3',4'-dichlorobenzoyl)-2,4-dihydro-3H-pyrazol-3-ylidene]bisphosphonic acid tetraethyl ester,
[5-(3',5'-dichlorobenzoyl)-2,4-dihydro-3H-pyrazol-3-ylidene]bisphosphonic acid tetraethyl ester,
[5-(2',6'-dichlorobenzoyl)-2,4-dihydro-3H-pyrazol-3-ylidene]bisphosphonic acid tetraethyl ester,
[5-(4'-fluorobenzoyl)-2,4-dihydro-3H-pyrazol-3-ylidene]bisphosphonic acid tetraethyl ester,
[5-(2',3',4',5',6''-pentafluorobenzoyl)-2,4-dihydro-3H-pyrazol-3-ylidene]bisphosphonic acid tetraethyl ester,
[5-(2'-methoxybenzoyl)-2,4-dihydro-3H-pyrazol-3-ylidene]bisphosphonic acid tetraethyl ester,
[5-(3',5'-dimethoxybenzoyl)-2,4-dihydro-3H-pyrazol-3-ylidene]bisphosphonic acid tetraethyl ester,
[5-(2'-chloro-4'-methoxybenzoyl)-2,4-dihydro-3H-pyrazol-3-ylidene]bisphosphonic acid tetraethyl ester,
[5-(4'-chloro-2'-methoxybenzoyl)-2,4-dihydro-3H-pyrazol-3-ylidene]bisphosphonic acid tetraethyl ester,
[5-(3'-chloro-4'-methoxybenzoyl)-2,4-dihydro-3H-pyrazol-3-ylidene]bisphosphonic acid tetraethyl ester,
[5-(4'-chloro-3'-methoxybenzoyl)-2,4-dihydro-3H-pyrazol-3-ylidene]bisphosphonic acid tetraethyl ester,
[5-(3'-methoxybenzoyl)-2,4-dihydro-3H-pyrazol-3-ylidene]bisphosphonic acid tetraethyl ester,
[5-(2'-ethoxybenzoyl)-2,4-dihydro-3H-pyrazol-3-ylidene]bisphosphonic acid tetraethyl ester,
[5-(3'-ethoxybenzoyl)-2,4-dihydro-3H-pyrazol-3-ylidene]bisphosphonic acid tetraethyl ester,
[5-(4'-ethoxybenzoyl)-2,4-dihydro-3H-pyrazol-3-ylidene]bisphosphonic acid tetraethyl ester,
[5-(2'-phenoxybenzoyl)-2,4-dihydro-3H-pyrazol-3-ylidene]bisphosphonic acid tetraethyl ester,
[5-(3'-phenoxybenzoyl)-2,4-dihydro-3H-pyrazol-3-ylidene]bisphosphonic acid tetraethyl ester,
[5-(4'-phenoxybenzoyl)-2,4-dihydro-3H-pyrazol-3-ylidene]bisphosphonic acid tetraethyl ester,
[5-(2'-methylthiobenzoyl)-2,4-dihydro-3H-pyrazol-3-ylidene]bisphosphonic acid tetraethyl ester,
[5-(3'-methylthiobenzoyl)-2,4-dihydro-3H-pyrazol-3-ylidene]bisphosphonic acid tetraethyl ester,
[5-(4'-methylthiobenzoyl)-2,4-dihydro-3H-pyrazol-3-ylidene]bisphosphonic acid tetraethyl ester,
[5-(2'-chloro-4'-methylbenzoyl)-2,4-dihydro-3H-pyrazol-3-ylidene]bisphosphonic acid tetraethyl ester,
[5-(4'-chloro-2'-methylbenzoyl)-2,4-dihydro-3H-pyrazol-3-ylidene]bisphosphonic acid tetraethyl ester,
[5-(3'-chloro-4'-methylbenzoyl)-2,4-dihydro-3H-pyrazol-3-ylidene]bisphosphonic acid tetraethyl ester,
[5-(4'-chloro-3'-methylbenzoyl)-2,4-dihydro-3H-pyrazol-3-ylidene]bisphosphonic acid tetraethyl ester,
[5-(2'-ethylbenzoyl)-2,4-dihydro-3H-pyrazol-3-ylidene]bisphosphonic acid tetraethyl ester,
[5-(3'-ethylbenzoyl)-2,4-dihydro-3H-pyrazol-3-ylidene]bisphosphonic acid tetraethyl ester,
[5-(4'-ethylbenzoyl)-2,4-dihydro-3H-pyrazol-3-ylidene]bisphosphonic acid tetraethyl ester,
[5-(4'-tert-butylbenzoyl)-2,4-dihydro-3H-pyrazol-3-ylidene]bisphosphonic acid tetraethyl ester,
[5-(2',4'-dimethylbenzoyl)-2,4-dihydro-3H-pyrazol-3-ylidene]bisphosphonic acid tetraethyl ester,
[5-(3',5'-dimethylbenzoyl)-2,4-dihydro-3H-pyrazol-3-ylidene]bisphosphonic acid tetraethyl ester,
[5-(2'-phenylbenzoyl)-2,4-dihydro-3H-pyrazol-3-ylidene]bisphosphonic acid tetraethyl ester,
[5-(3'-phenylbenzoyl)-2,4-dihydro-3H-pyrazol-3-ylidene]bisphosphonic acid tetraethyl ester,

[5-(4'-phenylbenzoyl)-2,4-dihydro-3H-pyrazol-3-ylidene]bisphosphonic acid tetraethyl ester,
[5-(4'-morpholinobenzoyl)-2,4-dihydro-3H-pyrazol-3-ylidene]bisphosphonic acid tetraethyl ester,
[5-(4'-dimethylaminobenzoyl)-2,4-dihydro-3H-pyrazol-3-ylidene]bisphosphonic acid tetraethyl ester,
[5-(4'-diethylaminobenzoyl)-2,4-dihydro-3H-pyrazol-3-ylidene]bisphosphonic acid tetraethyl ester,
[5-(1'-naphthoyl)-2,4-dihydro-3H-pyrazol-3-ylidene]-bisphosphonic acid tetraethyl ester,
[5-(2'-naphthoyl)-2,4-dihydro-3H-pyrazol-3-ylidene]-bisphosphonic acid tetraethyl ester,
[5-(6'-quinolinoyl)-2,4-dihydro-3H-pyrazol-3-ylidene]bisphosphonic acid tetraethyl ester,
[5-(8'-quinolinoyl)-2,4-dihydro-3H-pyrazol-3-ylidene]bisphosphonic acid tetraethyl ester,
[5-(2'-thienylcarbonyl)-2,4-dihydro-3H-pyrazol-3-ylidene]bisphosphonic acid tetraethyl ester,
[5-(2'-pyridylcarbonyl)-2,4-dihydro-3H-pyrazol-3-ylidene]bisphosphonic acid tetraethyl ester,
[5-(nicotinoyl)-2,4-dihydro-3H-pyrazol-3-ylidene]bisphosphonic acid tetraethyl ester,
[5-(4'-pyridylcarbonyl)-2,4-dihydro-3H-pyrazol-3-ylidene]bisphosphonic acid tetraethyl ester,
[5-(cyclobutanoyl)-2,4-dihydro-3H-pyrazol-3-ylidene]bisphosphonic acid tetraethyl ester and
[5-(cyclopentanoyl)-2,4-dihydro-3H-pyrazol-3-ylidene]bisphosphonic acid tetraethyl ester.

11. [5-(3'-Fluorobenzoyl)-2,4-dihydro-3H-pyrazol-3-ylidene]-bisphosphonic acid tetraethyl ester.

12. [5-(2',3',4'-Trichlorobenzoyl)-2,4-dihydro-3H-pyrazol-3-ylidene]bisphosphonic acid tetraethyl ester.

* * * * *